United States Patent [19]

Resnick

[11] 4,390,720
[45] Jun. 28, 1983

[54] ALKYL-ω-FLUOROFORMYL ESTER AND PROCESS

[75] Inventor: Paul R. Resnick, Wilmington, Del.

[73] Assignee: E. I. Du Pont de Nemours and Company, Wilmington, Del.

[21] Appl. No.: 311,312

[22] Filed: Oct. 14, 1981

[51] Int. Cl.³ .................. C07C 67/31; C07C 67/317; C07C 69/708

[52] U.S. Cl. ..................................... 560/184; 560/183

[58] Field of Search ......................................... 560/184

[56] References Cited

U.S. PATENT DOCUMENTS

| | | | |
|---|---|---|---|
| 3,274,239 | 9/1966 | Selman | 260/514 |
| 3,282,875 | 11/1966 | Connolly et al. | 260/29.6 |
| 3,308,107 | 3/1967 | Selman et al. | 260/87.5 |
| 3,321,517 | 5/1967 | Selman | 260/544 |
| 3,674,820 | 7/1972 | Pittman et al. | 560/184 |
| 3,847,978 | 11/1974 | Sianesi et al. | 260/535 H |
| 3,852,326 | 12/1974 | Nottke | 260/465.6 |
| 4,116,888 | 9/1978 | Ukihashi et al. | 521/31 |
| 4,126,588 | 11/1978 | Ukihashi et al. | 521/31 |
| 4,131,740 | 12/1978 | England | 560/180 |
| 4,138,373 | 2/1979 | Ukihashi et al. | 521/38 |
| 4,138,426 | 2/1979 | England | 260/465.6 |
| 4,176,215 | 11/1979 | Molnar et al. | 521/27 |
| 4,209,367 | 6/1980 | Seko et al. | 204/98 |
| 4,304,927 | 12/1981 | Krespan | 560/184 |

FOREIGN PATENT DOCUMENTS

| | | |
|---|---|---|
| 53-1692 | 1/1978 | Japan . |
| 56-47332 | 11/1981 | Japan . |
| 2058763A | 4/1981 | United Kingdom . |

Primary Examiner—Natalie Trousof
Assistant Examiner—L. Hendriksen
Attorney, Agent, or Firm—James A. Costello

[57] ABSTRACT

Process for making alkyl-ω-fluoroformyl esters of the formula

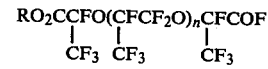

wherein R is $CH_3$ or $C_2H_5$ and n is 0 or an integer from 1 to 3, by reacting the methyl or ethyl ester of trifluoropyruvic acid with hexafluoropropene oxide in the presence of fluoride ion catalyst, in an aprotic liquid medium; and the ester wherein n=0.

16 Claims, No Drawings

ALKYL-ω-FLUOROFORMYL ESTER AND PROCESS

BACKGROUND OF THE INVENTION

This invention relates to perfluorinated alkyl-ω-fluoroformyl carboxylate intermediates to carboxy-functional fluorovinyl ethers and copolymers thereof.

Great Britain Application No. 2,058,763A discloses methyl trifluoropyruvate and a process for making it.

U.S. Pat. Nos. 3,847,978 and 4,131,740, and EPO Publication No. 0013122 disclose acid fluorides. They do not, however, disclose the acid fluoride of this invention, nor do they suggest the process of this invention for making acid fluorides.

U.S. Pat. Nos. 4,116,888, 4,126,588, 4,138,373, and 4,138,426 disclose fluorinated vinyl ether monomers made from certain acid fluoride intermediates.

U.S. Pat. Nos. 3,282,875, 4,176,215, and 4,209,367 disclose certain fluorinated vinyl ether monomers, copolymers made from them, and various utilities for said copolymers including use as ion exchange membranes and the like.

U.S. Pat. Nos. 3,308,107 and 3,321,517 disclose the reaction of trifluoropyruvyl fluoride, $CF_3C(O)C(O)F$, with HFPO to form cyclic dioxanes, and U.S. Pat. No. 3,274,239 discloses reaction of fluorinated ketones, $XR_FC(O)R'_FX'$, with HFPO to form linear fluoroformyl-terminated adducts; $R_F$ and $R_F'$ are perfluoroalkylene and X, X' are H or halogen.

J53/1692 discloses fluorinated cation-exchange copolymers containing units from the vinyl ether monomer, $CF_2=CXOCFX'A$, wherein X is F or $CF_3$, X' is F or perfluoroalkyl of $C_{1-10}$, and A includes $-CO_2R$. The reference describes the primary carboxylate, $CF_2=CFOCF_2CO_2R$, prepared by pyrolyzing the acyl fluoride,

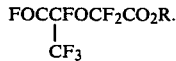

The latter is prepared from oxalyl fluoride by reaction with an alcohol (ROH) and HFPO.

Finally, U.S. Pat. No. 3,852,326 discloses secondary-nitrile-containing acid fluorides and their conversion to vinyl ether monomers.

SUMMARY OF THE INVENTION

The alkyl-ω-fluoroformyl esters obtained by the process of this invention have the formula:

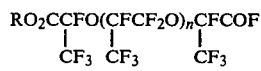

wherein R is $CH_3$ or $C_2H_5$ and n is 0 or an integer from 1 to 3, preferably 0 or 1. The ester wherein n=0 is a compound of this invention.

Such esters, also referred to herein as HFPO adducts or acid fluorides, are made by reacting the methyl or ethyl ester of trifluoropyruvic acid

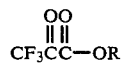

with hexafluoropropene oxide (HFPO) in the presence of fluoride ion catalyst, in an aprotic liquid medium.

The esters can be converted by pyrolysis into vinyl ethers of the formula

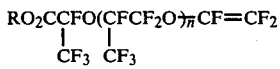

which can be copolymerized with one or more fluorinated monoolefins such as tetrafluoroethylene to copolymers useful as ion-exchange membranes.

DETAILS OF THE INVENTION

The starting reactant(s) for the process of this invention can be made as follows:

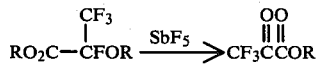

wherein R is $CH_3$ or $C_2H_5$. Further details concerning reaction conditions, especially with regard to the methyl esters, are described in Great Britain application No. 2,058,763A. Preparation of these starting reactants forms no part of the instant invention.

The fluoride ion catalyst can be provided by an alkali metal fluoride such as CsF, KF, $NH_4F$, or a tetraalkyl ammonium fluoride (alkyl of 1 to 4 carbon atoms), or a sulfonium fluoride such as benzene sulfonium fluoride. Potassium fluoride is preferred because its use results in improved yields of desired products. The fluoride catalyst can be used in amounts of about 0.001 to 1.0 molar equivalent per mole of pyruvate.

Suitable reaction media are aprotic organic liquids, or mixtures thereof, including the so-called glymes (mono-, di-, tri- and tetraethylene glycol dimethyl ether); mononitriles such as aceto-, propio-, butyro- and benzonitrile; dinitriles such as malono-, succino-, glutaro-, adipo-, methylmalono-, pimelo-, subero- and phthalonitrile; nitrobenzenes; lactones such as γ-butyrolactone, δ-valerolactone and δ-caprolactone; and perfluorinated ethers.

Preferred liquids are mixtures of dinitriles and glymes; especially preferred are mixtures of adiponitrile and tetraglyme in the proportion of about 60 to 98 weight percent of adiponitrile and 2 to 40 weight percent of tetraglyme.

Aprotic liquids and liquid mixtures useful in the process of preparing the HFPO adducts(s) are those capable of dissolving, to varying extents, the fluoride catalyst, the trifluoropyruvate esters and the HFPO adduct(s). Adduct solubility tends to decrease in a given medium as the value of n increases. Therefore, correspondingly higher dissolving power is needed to dissolve adducts containing higher proportions of HFPO.

It is a facet of this invention that the proportion of glyme to nitrile (when such a mixed liquid medium is employed) can be adjusted to control whether the process will favor formation of esters wherein n is 0 or 1 or esters wherein n is 2 or 3. The dissolving power of nitrile/glyme mixtures increases with increasing glyme content. Thus, mixtures containing about 60 to 80 weight percent of nitrile favor formation of esters wherein n is 2, 3 and above while mixtures containing higher proportions of nitrile, to about 98 weight percent, favor formation of esters wherein n is 0 or 1.

Choice of liquid also influences the rate at which the adducts are formed by controlling the amount of catalyst in solution. Fluoride ion sources such as potassium fluoride are more soluble in the glymes than in the nitriles. Thus, glyme/nitrile mixed solvents can be tailored for preferred adducts and for optimum reaction rate. Higher rates of adduct formation also improve adduct yields by suppressing an HFPO oligomer-forming side reaction. The liquid or liquid mixture employed as the reaction medium should be capable of dissolving at least about 0.001 molar equivalent of fluoride compound per mole of pyruvate ester reactant.

In preparing preferred adducts wherein n is 0 or 1, it has been found that the reaction proceeds best when a substantial molar excess of the pyruvate over HFPO is used, and when a liquid medium is selected in which the solubility of the desired adduct, and all higher adducts, is relatively low. Under such conditions, the desired adduct is removed from solution so that it does not react further with HFPO. In the reaction of the pyruvate with two moles of HFPO to form the adduct wherein n=1, inevitably the monoadduct (n=0) is also formed as an intermediate and must be at least partly soluble in the reaction mixture so as to react with a further mole of HFPO. The monoadduct so formed can be recycled into the claimed process, either alone or admixed with pyruvate. Such a mixture can be prepared by adding fresh pyruvate to the reaction vessel or by recovering the monoadduct and mixing it with a fresh charge of excess pyruvate and HFPO in a subsequent reaction. Other methods of assuring product optimization will be obvious to one skilled in the art from the description provided herein.

Use of excess pyruvate improves yields of the desired lower adducts (n=0, 1) as well as overall yields of adducts by helping to suppress formation of HFPO oligomers which are normally undesired by-products.

Reaction temperatures between 25° and 70° C. are preferred. Pressure is not critical, and subatmospheric and superatmospheric pressures are operable; pressures close to atmospheric are preferred. As illustrated in the Examples, pressure in the reaction vessel is normally controlled by regulating the supply of gaseous HFPO. Also, relatively high temperatures and low HFPO pressures (within the parameters described herein) tend to favor production of adducts where n is 0 or 1. On the other hand, to obtain adducts wherein n is 2 or 3, it is desirable to employ relatively low temperature and high HFPO pressure.

The acyl fluoride products can be pyrolyzed over a solid basic salt such as trisodium phosphate, potassium carbonate, or, preferably, sodium carbonate, to obtain corresponding polymerizable vinyl ether monomers:

$$RO_2CCFO(CFCF_2O)_nCFCOF \xrightarrow{\Delta}$$
$$\phantom{RO_2CC}|\phantom{FO(C}|\phantom{FCF_2O)_n}|$$
$$\phantom{RO_2CC}CF_3\phantom{F}CF_3\phantom{(CFCF_2O)_n}CF_3$$

$$RO_2CCFO(CFCF_2O)_nCF=CF_2$$
$$\phantom{RO_2CC}|\phantom{FO(C}|$$
$$\phantom{RO_2CC}CF_3\phantom{F}CF_3$$

The pyrolysis reaction takes place at temperatures of about 120° C. to 300° C., preferably 150° C. to 250° C., in an inert atmosphere, e.g., nitrogen, in the presence of the basic salts which have been previously dried by heating to at least about 300° C. The depicted monomeric diesters and copolymers prepared therefrom can be converted by known methods into fluorovinyl ether monomers or copolymers possessing such functionality as:

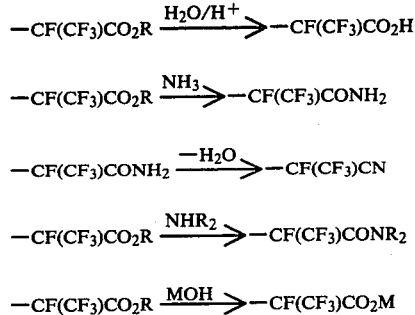

wherein R and M are as defined previously.

The monomers and derivatives thereof can be copolymerized with one or more fluorinated vinyl monomers to yield solid, tough thermoplastic copolymers which can be molded into shaped articles, including films, and ion exchange membranes for chloralkali electrolysis cells. Copolymers containing —CN functions, introduced by post-reaction of the monomer or its copolymer, are especially useful for incorporating cure sites into fluoroelastomer compositions. Preparation and use of such copolymers are described more fully in U.S. Pat. Nos. 3,282,875, 4,176,215 and 4,209,367.

In the following Examples of specific embodiments of this invention, parts and percentages are by weight and temperatures are in degrees Celsius, unless otherwise specified.

EXAMPLE 1

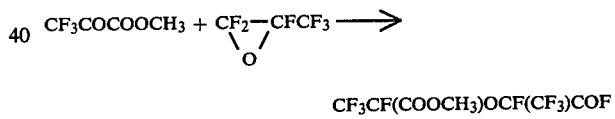

$$CF_3CF(COOCH_3)OCF(CF_3)COF$$

Potassium fluoride (5 g) in a 2 liter 3-neck flask was heated by a Meker burner under vacuum with swirling to dryness. After cooling, the flask was filled with nitrogen and fitted with a thermometer and large magnetic stirrer. Then, 20 ml of tetraglyme was added, the flask was evacuated and flushed with nitrogen. Methyl trifluoropyruvate (38 g, 0.24 m) was added and the flask was evacuated, filled with HFPO and weighed. Stirring was started and HFPO was absorbed exothermally (maximum 60°). Pressure of HFPO was maintained at about 700 mm. After 68 g (0.41 m) of HFPO was absorbed the reaction was stopped and volatiles recovered under about 1 mm vacuum to a liquid nitrogen-cooled trap while heating the reaction vessel in a steam bath. Material recovered in the trap (103.5 g) was distilled to give about 12 g of HFPO dimer, 10 g of HFPO trimer, 25 g of recovered methyl trifluoropyruvate, 21.5 g of monoadduct, bp 113°, and 21 g of high boiling material attributed to higher HFPO adducts including n=2,3.

For the monoadduct: IR: 5.30 (COF) and 5.58 (COOCH$_3$). Anal. Calcd. for $C_7H_3F_9O_4$: C, 26.10; H, 0.94; F, 53.09. Found: C, 26.52; H, 0.97; F, 50.52.

EXAMPLE 2

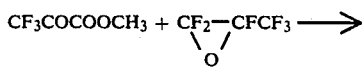

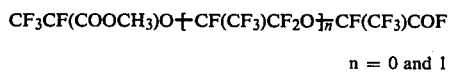

n = 0 and 1

The reaction was carried out as described in Example 1 using 5 g of potassium fluoride, 55 g of methyl trifluoropyruvate and, in place of tetraglyme, a mixture of 26 g of adiponitrile and 1.3 g of tetraglyme. Absorption of HFPO was slow and was stopped after addition of 135 g. There was recovered 188 g to distill. The distillation yielded 50 g of HFPO dimer, 25 g of HFPO trimer, 25 g of recovered methyl trifluoropyruvate, 35 g of monoadduct, bp 112°, 18 g of diadduct, bp 48° to 52°/9.5 mm, and 35 g of high boiling material attributed to higher HFPO adducts including n=2,3.

For the diadducts: IR: 5.30 (COF) and 5.58 (COOCH$_3$). Anal. Calcd. for $C_{10}H_3F_{15}O_5$: C, 24.60; H, 0.62; F, 58.39. Found: C, 24.88; H, 0.66; F, 58.71.

Making Monomer

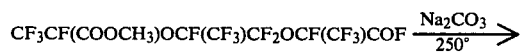

A. The acid fluoride (25 ml, 42.5 g), prepared as in Example 2, was added dropwise from a syringe driven by a Sage pump at a rate of 0.6 ml/min in a slow current of nitrogen to a stirred bed of 90 ml of dry sodium carbonate heated to 250°. When addition was complete, product was recovered from the bed in a Dry Ice ®-cooled trap with vacuum applied. Distillation of the crude product (32.5 g) gave 22 g of the above vinyl ether, bp 48°/11 mm.

IR: 5.40 (OCF=CF$_2$) and 5.58 (COOCH$_3$). Anal. Calcd. for $C_9H_3F_{13}O_4$: C, 25.61; H, 0.72; F, 58.51. Found: C, 25.79; H, 1.31; F, 59.77.

B. The reaction in Part A was repeated on 75 g (45 ml) of the acid fluoride through a 90 ml stirred bed of trisodium phosphate at 250° in place of sodium carbonate. Another 78 g (47 ml) sample of the acid fluoride was passed through a fresh 90 ml bed of trisodium phosphate. The two crude products (61 g and 65 g) were distilled together to give 90 g of the vinyl ether, bp 65°/30 mm.

Making Copolymer

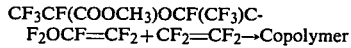

A mixture of 5 ml of F-113 (1,1,2-trichlorotrifluoroethane), 5.08 g of the above vinyl ether, 6 g of tetrafluoromethylene and 20 l of 6% perfluoropropionylperoxide was sealed in a 50 ml Carius tube which was rotated at room temperature overnight.

After cooling in liquid nitrogen, the tube was opened, evacuated to a trap cooled in liquid nitrogen and warmed with hot air. There was recovered 15.5 g of volatiles which lost 3 g (tetrafluoroethylene) in coming to room temperature. There was recovered from the tube 3.6 g of polymer (3.3 g after washing with F-113 and drying). Infrared absorption of a film of the polymer pressed between salt plates showed the presence of COOCH$_3$ in the copolymer.

EXAMPLE 3

The reaction was carried out as described in Example 1 using 2 g of potassium fluoride, 25 g of methyl trifluoropyruvate and, in place of tetraglyme, a mixture of 38 ml of adiponitrile, 10 ml of tetraglyme, and 30 grams of Rimar 101 perfluorinated ethers. Absorption of HFPO was slow. A total of 68 g of HFPO was added. The reaction mixture was filtered. The filtrate weighed 162.0 g (93.5% recovery) and consisted of two layers which were separated; upper layer 46.8 g, lower layer 115 g. The lower layer was analyzed by gas chromatography using a 5.5 m by 6.35 mm diameter column packed with a support of white diatomaceous earth (Gas-chrom ® Z, Applied Science Co.) carrying 20 weight percent of 3,3,3-trifluoropropylsilicone, starting at room temperature and heated at 10° C./min. Approximately 23 g of monoadduct (n=0) and 5 g of diadduct were obtained, together with 53 g of HFPO oligomers, 5 g of unreacted methyl trifluoropyruvate, and a high boiling residue of about 1 g attributed to higher adducts (n≧2).

The products were determined to be as depicted above (wherein n=0,1) based primarily on gas chromatographic retention times. Gaseous effluent from the chromatographic column corresponding to the monoadduct was collected in an Orsat gas bag. The IR spectrum of this effluent was weak, with bands at 5.49, 5.52 and 5.60$\mu$.

The embodiments of the invention in which an exclusive property or privilege is claimed are defined as follows:

1. A process for making esters of the formula $$RO_2CCFO(CFCF_2O)_nCFCOF$$
$$\phantom{RO_2CC}|\phantom{FO(C}|\phantom{FCF_2O)_nC}|$$
$$\phantom{RO_2CC}CF_3\phantom{F}CF_3\phantom{CF_2O)_n}CF_3$$

wherein R is CH$_3$ or C$_2$H$_5$ and n is 0 or an integer from 1 to 3, comprising reacting the methyl or ethyl ester of trifluoropyruvic acid with hexafluoropropene oxide in the presence of fluoride ion catalyst, in an aprotic liquid medium.

2. A process according to claim 1 comprising employing the methyl ester of trifluoropyruvic acid.

3. A process according to claim 1 comprising employing the ethyl ester of trifluoropyruvic acid.

4. A process according to any one of claims 1, 2 or 3 comprising employing a fluoride ion catalyst selected from the group consisting of alkali metal fluoride, ammonium fluoride, tetraalkyl ammonium fluoride, and sulfonium fluoride.

5. A process according to claim 4 comprising employing the catalyst in an amount of about 0.001 to 1.0 molar equivalent per mole of the ester of trifluoropyruvic acid.

6. A procss according to claim 4 comprising employing potassium fluoride as the fluoride ion catalyst.

7. A process according to claim 4 comprising employing, as the aprotic liquid medium, a mixture of an ethylene glycol dimethyl ether and a nitrile.

8. A process according to claim 7 wherein the ether is tetraethylene glycol dimethyl ether and the nitrile is adiponitrile.

9. A process according to claim 8 wherein the proportions of adiponitrile and ether are about 60 to 98 weight percent and about 2 to 40 weight percent, respectively.

10. A process according to claim 9 wherein the proportions of adiponitrile and ether are about 60 to 80 weight percent and about 20 to 40 weight percent, respectively.

11. A process according to claim 9 wherein the proportions of adiponitrile and ether are about 80 to 98 weight percent and about 2 to 20 weight percent, respectively.

12. A process according to claim 7 comprising the additional step of adjusting the relative proportion of ethylene glycol dimethyl ether to nitrile in the liquid medium thereby favoring formation of esters wherein n is 0 or 1 or favoring formation of esters wherein n is 2 or 3.

13. A process according to claim 12 wherein the proportion of ethylene glycol dimethyl ether to nitrile is adjusted to favor formation of esters wherein n is 0 or 1.

14. A process according to claim 12 wherein the proportion of ethylene glycol dimethyl ether to nitrile is adjusted to favor formation of esters wherein n is 2 or 3.

15. A process according to claim 1 comprising the additional step of pyrolyzing the esters to form vinyl ether monomers of the formula $$RO_2CCFO(CFCF_2O)_nCF=CF_2.$$
$$\phantom{RO_2CCFO(}|\phantom{CFCF_2O)_n}|$$
$$\phantom{RO_2CCFO(}CF_3\phantom{CF_2O)_n}CF_3$$

16. An ester of the formula:

$$RO_2CCFOCFCOF$$
$$\phantom{RO_2CC}|\phantom{OC}|$$
$$\phantom{RO_2CC}CF_3\phantom{O}CF_3$$

wherein R is $CH_3$ or $C_2H_5$.

* * * * *